United States Patent
Wachemig et al.

(10) Patent No.: US 9,939,363 B2
(45) Date of Patent: Apr. 10, 2018

(54) PARTICLE TRACKING ANALYSIS METHOD USING SCATTERED LIGHT (PTA) AND DEVICE FOR DETECTING AND IDENTIFYING PARTICLES OF A NANOMETRIC ORDER OF MAGNITUDE IN LIQUIDS OF ALL TYPES

(71) Applicant: PARTICLE METRIX GMBH, Meerbusch (DE)

(72) Inventors: Hanno Wachemig, Diessen a.A. (DE); Margret Boeck, Meerbusch (DE)

(73) Assignee: PARTICLE METRIX GMBH, Meerbusch (DE)

( * ) Notice: Subject to any disclaimer, the term of this patent is extended or adjusted under 35 U.S.C. 154(b) by 0 days.

(21) Appl. No.: 15/305,401

(22) PCT Filed: May 12, 2015

(86) PCT No.: PCT/DE2015/000241
§ 371 (c)(1),
(2) Date: Oct. 20, 2016

(87) PCT Pub. No.: WO2015/176698
PCT Pub. Date: Nov. 26, 2015

(65) Prior Publication Data
US 2017/0059471 A1 Mar. 2, 2017

(30) Foreign Application Priority Data
May 19, 2014 (DE) .................. 10 2014 007 355

(51) Int. Cl.
*G01N 21/00* (2006.01)
*G01N 15/14* (2006.01)
(Continued)

(52) U.S. Cl.
CPC ..... *G01N 15/1463* (2013.01); *G01N 15/0211* (2013.01); *G01N 15/0227* (2013.01);
(Continued)

(58) Field of Classification Search
CPC .. G02B 21/06; G02B 21/365; G01N 15/1436; G01N 15/0205; G01N 15/04;
(Continued)

(56) References Cited

U.S. PATENT DOCUMENTS

| 3,764,512 A | 10/1973 | Greenwood et al. |
| 4,180,739 A | 12/1979 | Abu-Shumays |

(Continued)

FOREIGN PATENT DOCUMENTS

| CN | 102593711 | 7/2012 |
| DE | 69123957 | 4/1997 |

(Continued)

OTHER PUBLICATIONS

Tan, "Effects of Carbon Loading on the Performance of Functionalized Carbon Nanotube Polymer Heat Sink for High Power Light-Emitting Diode in Switching Applications", IEEE Transactions of Nonotechnology, US, IEEEE, Aug. 29, 2013, vol. 12, No. 6, pp. 1104-1110.

(Continued)

*Primary Examiner* — Hoa Pham
(74) *Attorney, Agent, or Firm* — Duane Morris LLP; Gregory M. Lefkowitz; Jason M. Nolan

(57) ABSTRACT

A method and device for optically detecting particles, including: (a) a cell wall of rectangular cross-section is fitted on a longitudinal surface and adjoining transverse surface with an L-shaped heating and cooling element; (b) the center of the transverse surface of the cell wall opposite the transverse surface which forms the support of the cell wall is irradiated by an irradiation device and is observed at right (Continued)

angles to the optical axis of the irradiation device; (c) the focus of the irradiation device and the observation device can be moved by a motor to any point in the three-dimensional inner region defined by the cell wall; (d) the surface of the cell wall opposite the optical glass window through which the radiation from the irradiation device enters comprises another optical glass window; (e) the temperature of the surface of the cell wall is monitored by two thermistors.

12 Claims, 5 Drawing Sheets

(51) Int. Cl.
| | | |
|---|---|---|
| G01N 15/02 | (2006.01) | |
| G01N 21/03 | (2006.01) | |
| G01N 27/447 | (2006.01) | |
| G01N 21/51 | (2006.01) | |
| G02B 21/06 | (2006.01) | |
| G02B 21/36 | (2006.01) | |
| H04N 5/77 | (2006.01) | |
| G06T 7/70 | (2017.01) | |
| G01N 15/00 | (2006.01) | |
| G01N 15/10 | (2006.01) | |
| G01N 21/47 | (2006.01) | |

(52) U.S. Cl.
CPC ..... *G01N 15/1436* (2013.01); *G01N 21/0332* (2013.01); *G01N 21/51* (2013.01); *G01N 27/44752* (2013.01); *G02B 21/06* (2013.01); *G02B 21/365* (2013.01); *G06T 7/70* (2017.01); *H04N 5/772* (2013.01); *G01N 2015/0038* (2013.01); *G01N 2015/0053* (2013.01); *G01N 2015/0222* (2013.01); *G01N 2015/0238* (2013.01); *G01N 2015/1075* (2013.01); *G01N 2021/4726* (2013.01); *G01N 2201/06113* (2013.01); *G06T 2207/10056* (2013.01)

(58) Field of Classification Search
CPC ........... G01N 15/1463; G01N 15/0227; G01N 15/0211; G01N 21/0332; G01N 21/51; G01N 2/44721; G01N 2/44734; G01N 2/44752
USPC .................................................. 356/335–343
See application file for complete search history.

(56) References Cited

U.S. PATENT DOCUMENTS

| | | | |
|---|---|---|---|
| 4,242,194 A | | 12/1980 | Steiner et al. |
| 4,456,513 A | * | 6/1984 | Kawai ................. G01N 27/447 204/400 |
| 2007/0163884 A1 | | 7/2007 | Strand et al. |
| 2012/0002029 A1 | | 1/2012 | Sieracki et al. |

FOREIGN PATENT DOCUMENTS

| | | |
|---|---|---|
| DE | 102006028516 | 10/2007 |
| DE | 102008007743 | 5/2009 |
| GB | 1528845 | 10/1978 |
| JP | S555240 | 1/1980 |
| JP | S57122347 | 7/1982 |
| JP | H11218485 | 8/1999 |
| JP | 2006177964 | 7/2006 |
| JP | 2012058053 | 3/2012 |
| WO | 92/07244 | 4/1992 |
| WO | 2013/061312 | 5/2013 |

OTHER PUBLICATIONS

Kim et al., :Raman Characterization of Thermal Conduction in Transparent Carbon Nanotube Films, Langmuir, U.S. American Chemical Society, Oct. 17, 2011, vol. 27, pp. 14532-14538.

* cited by examiner

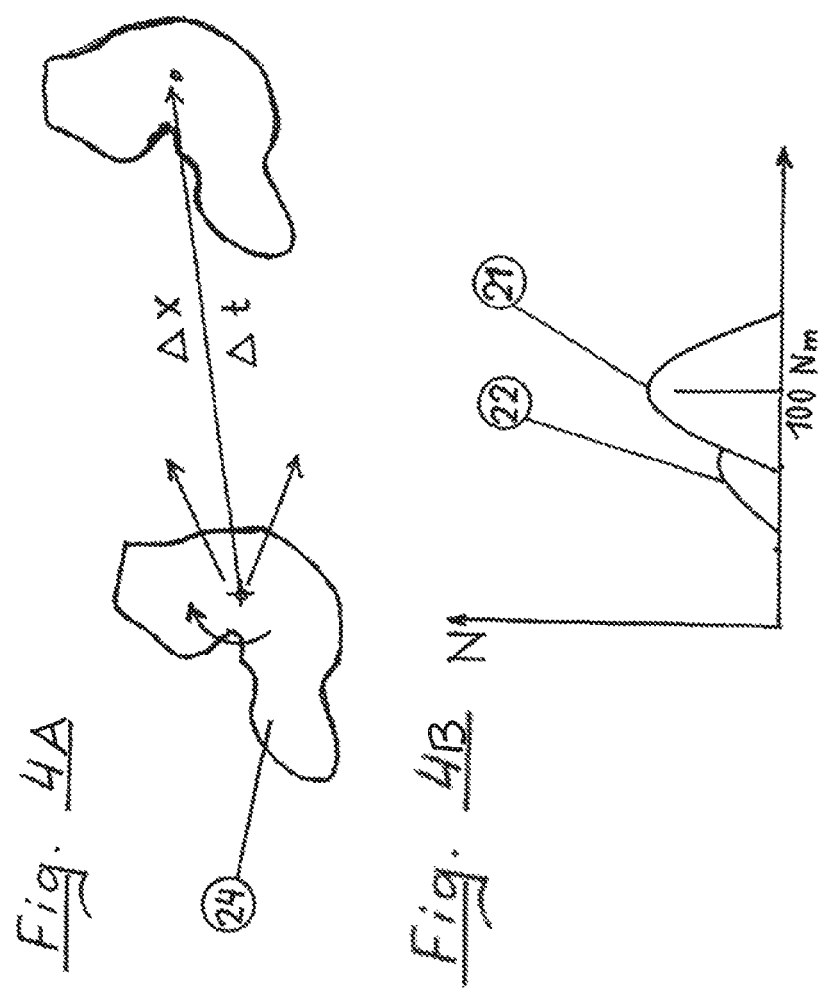

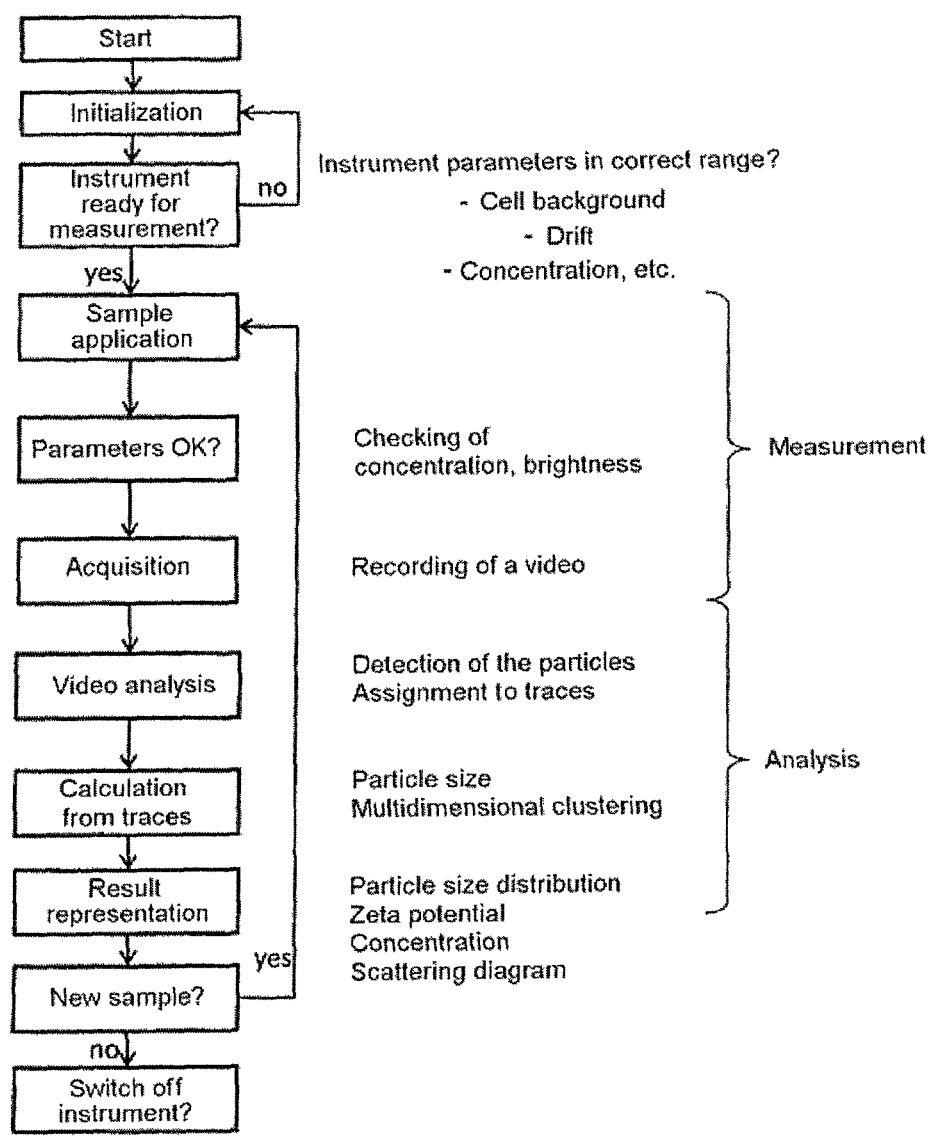

PARTICLE TRACKING ANALYSIS METHOD USING SCATTERED LIGHT (PTA) AND DEVICE FOR DETECTING AND IDENTIFYING PARTICLES OF A NANOMETRIC ORDER OF MAGNITUDE IN LIQUIDS OF ALL TYPES

CROSS-REFERENCE TO RELATED APPLICATIONS

This application is a §371 national stage entry of International Application No. PCT/DE2015/000241, filed May 12, 2015, which claims priority to German Patent Application No. 10 2014 007 355.6 filed May 19, 2014, the entire contents of which are incorporated herein by reference.

BACKGROUND OF THE INVENTION

The invention relates to a method of particle tracking analysis with the aid of scattered light and to an apparatus for detecting and characterizing particles in liquids of all types of the order of magnitude of nanometers.

Suspensions and emulsions as disperse material systems are often occurring forms of particles in liquids. Their uses range from printer ink through cosmetic emulsions to new materials such as quantum dots. Furthermore, nanobubbles, particles in waters, particles in pharmaceutical administrations and exosomes—i.e. nanoparticles with a messenger function released by body cells—are to be included as particles in liquids. The particles occur as individual originally occurring objects or as accumulations in the form of agglomerates or aggregates. In agglomerates, the individual constituents have a loose connection to one another, while aggregates can only be separated from one another by strong forces, for example by grinding processes. There is a great interest in quantifying the particles in their size and shape, and as an agglomerate or aggregate, and quantitatively detecting mixtures thereof. In the field of imaging methods, this is possible with an optical microscope up to a size of a few hundreds of nm, and with an electron microscope up to a minimum size of a few nm. In no method, however, is it yet possible to distinguish between agglomerates and aggregates. Electron microscopic examination suffers from the elaborate sample preparation, and the duration and cost of the analysis.

In contrast to optical microscopy and electron microscopy, optical scattered light analysis is an indirect measurement method for characterization of the particle size. It is used because particles of less than 1 μm (1000 nm) are not compatible with direct observation because of the diffraction limitation.

In a scattered light microscope, the light scattered by particles is used for localization of the particles and tracking of their movement in a video film. There are two versions of scattered light microscopes: the dark-field scattered light microscope with white light illumination and the dark-field laser scattered light microscope with laser illumination (dealt with below).

By analysis of the translational Brownian diffusion movement of each individual particle and subsequent conversion of the measured diffusion constants for each individual particle into the particle size by the Stokes-Einstein formula, the particle size distribution is derived.

When an electric field is applied to the disperse material system, the electrophoretic migration movement is additionally obtained, and therefrom the electric charge at the particle interface with the surrounding liquid. With the aid for example of the Smoluchowski formula, the measured electrophoretic mobility is converted into the so-called zeta potential. In this regard, there is the following consideration:

Disperse systems are, as is known, to be categorized among thermodynamically unstable systems. The time period over which such dispersions remain stable is of essential importance for usability. One instability very often to be observed results from coagulation of particles, which can lead to irreversible particle size growth, or to full separation between the liquid phase and the particle phase. Several precautions are used to reduce coagulation. One of these is electrostatic stabilization. In this case, use is made of the fact that the approach of particles charged in the same way is made difficult by their electrostatic repulsion. This repulsion is commensurately more efficient when the ionic charge of the particles on their interface with the medium is higher. Of crucial importance for this is the electrostatic particle interface potential "PIP", in particular the zeta potential often derived from the electrophoretic movement (see above). This potential is regarded as a measure which determines the degree of repulsion between neighboring dispersed particles. It therefore has importance in terms of the stability of disperse systems.

In the scattered light arrangements described above, the sample is externally at rest, and only the particles inside the sample move typically according to their size and shape.

The effect of particles resides inter alia in their order of magnitude. For instance, the brilliance of a color may be dependent inter alia on the size distribution, and the site of the effect of a pharmaceutical administration on the size of the carrier particle, for example of a liposome droplet or of gold particles coated with proteins.

Furthermore, the size of particles gives information about their quality, uniformity and usability. If, for example, there are too many agglomerates of a type of particle (protein) present or other types of substances are admixed, then the usability is called into question.

The particle shape also represents an important discriminating feature. In homogenized milk, for example, the fat droplets are broken up to the size of the casein particles of 300 nm. The difference between the two components consists only in the shape. In conventional size measurement methods of DLS, dynamic light scattering, disk centrifuging and ultrasound spectroscopy, fat droplets and casein cannot be distinguished from one another. The particle shape of particles below a size of about 1 μm has to date been measurable only with the aid of electron microscopy. Albeit only statistically and after enormous sample preparation. Dynamic in-situ observation of the particles in the carrier liquid is not possible.

The uncertainty about the correctness of the result of a size distribution is therefore related in conventional DLS scattered light methods to the fact that the scattered light coming from the scattered light volume is collectively gathered on a single detector element. The fluctuation of the scattered light signal is employed for the size distribution. In this case, it is not possible to distinguish whether the fluctuation is caused by the translational movement of the particles, on which the calculation of the particle size by conversion with the aid of the Stokes-Einstein equation is based, or by the rotation of unshaped particles. This is because the center-of-mass variations of a rotating particle aggregate contribute for example to the collective scattered light signal and lead to a "parasitic" fine component, which however cannot be identified per se. An additional uncertainty occurs in the case of substance mixtures, the scattered light behavior of which is different. In the case of substance mixtures, a misevaluation of the various components therefore occurs. If the particles of the different substances are of equal size, it firstly cannot even be suspected that more than one substance type is present in the sample, and even less which components thereof are present.

In electron microscopy as an imaging method, the shape can be measured. However, agglomerates cannot be distinguished from aggregates.

It is therefore desirable to develop a method which offers pattern recognition in a similar way to an electron microscope, but which is substantially fast and more economical and involves only little risk of sample modification by the preparation of the sample for measurement.

Furthermore, it is desirable to distinguish as many features as possible from discrete analysis of the individual particles, which are tracked by video film. Specifically, during the positional change of the particles, sometimes even out of the microscope focus, the particles adopt a constantly changing orientation with respect to the observing microscope. High-intensity vibrations of the individual particles are then found. All these phenomena are admittedly regarded classically as a difficulty of the particle tracking measurement method. Regarded positively, however, these difficulties offer the immense opportunity of a) distinguishing translation of the particles from rotation and thereby eliminating parasitic fine components and b) deriving a set of additional information from the dynamic behavior of the particles during their passage in the video film. This differs from the other methods such as DLS, electron microscopy and disk centrifuging.

In this invention, dynamic multiparameter analysis is thus used as an advantage in order to obtain even more valuable information than previously possible from the dynamics described.

One great difficulty in the PTA method remains the fact that it is necessary to produce an enormously high light contrast (signal/noise ratio in the video detector) for the analysis of nanoparticles. This is because the light scattering of nanoparticles decreases by more than the 6th power toward smaller diameters. Above all, it is necessary to ensure that the light contrast of the weakly luminous particles with respect to the background is maximal and is not attenuated by scattered light. With one sensitive camera alone, this is not achieved. In a scattered light arrangement, there is always parasitic light due to reflections of the exciting laser light at edges and cell walls, and this light also finds its way somehow into the video camera. Comparison with the optimal black night sky during star observation is obvious. The invention of measures for contrast improvement is used to be able to carry out the dynamic pattern recognition on nanoparticles in a size range which is as wide as possible.

Another difficulty with the PTA measuring technique results from the fact that only a small size measurement range of at most 8 to 1 can be recorded simultaneously with one camera setting. In the case of samples with a wider particle size distribution, up to 3 sample dilution stages a 1:3 to 1:4 with up 3 different camera settings are necessary. Dilution automation combined with an intuitive camera setting would substantially simplify the measurement and make it almost error-free in terms of operation. The additional fitting of a miniature pH probe is a further step in the direction of automation. Most users of PTA involve biochemically medical diagnosis. This involves very small sample quantities and often personnel who have difficulties with new types of analysis methods. In the case of samples with the need to measure the zeta potential, it is important to measure and register the ionic properties of the surrounding liquid. The two important parameters which characterize the ionic state in the vicinity of the particle interface are conductivity and pH. They should jointly be registered automatically and without intervention by personnel.

DE 10 2008 007 743 B3, in the name of the same Applicant, describes a method and an apparatus which relate to the detection of the particle distribution in liquids.

It is pointed out here that there are various physical methods for measuring the PIP.

In the prior art, reference is made in this regard inter alia to the U.S. Pat. No. 3,764,512 A, which discloses an apparatus for the optical detection of particles of a suspension in a cuvette 14, having the following features:
  a) the cuvette is positioned in a defined way by means of a mount,
  b) the cuvette is irradiated by means of an optical irradiation device and observed at a right angle to the optical axis of the irradiation device by an observation device,
  c) the position of the focus of the irradiation device and the position of the focus of the observation device can respectively be displaced in a motorized fashion over the spatial inner region of the cuvette, or by means of focusing adjustment.

This apparatus has the disadvantage that the optical arrangement is to be focused manually by manually adapting the two focal positions to one another until the image is seen as sharp.

In order to avoid these disadvantages, in DE 10 2008 007 743 B3 according to patent claim 1, an apparatus for the optical detection of particles of a suspension in a cuvette (1) having the following features is protected:
  a) the cuvette is positioned in a defined way by means of a mount,
  b) the cuvette is irradiated by means of an optical irradiation device and observed at a right angle to the optical axis of the irradiation device by an observation device,
  c) the focus of the irradiation device and the focus of the observation device can be displaced in a motorized fashion over the spatial inner region of the cuvette to an arbitrary point by a control apparatus,
  d) an approach of the position of the focus of the irradiation device to the position of the focus of the observation device, or vice versa, for the purpose of focusing at a point is monitored in a detection apparatus and/or represented on a display screen.

Although this method is universally usable, during the measurement of nanoparticles by scattered light or fluorescent light it is limited by the stray light background.

BRIEF SUMMARY OF THE INVENTION

The object of the apparatus according to the invention, or the method on which it is based, is to minimize the stray light background.

This object is achieved by:

An apparatus for detecting and characterizing particles (23) in liquids of all types of the order of magnitude of nanometers of a suspension in a cell wall (9), having the following features:
a) a cell wall (9) of rectangular cross section made of black glass with optical windows (11) sintered in has an L-shaped heating and cooling element (1) applied to a longitudinal face and an adjoining transverse face, the cell wall (9) bearing on the transverse face on a stand base (2) which is mounted in a defined way by means of vibration dampers (4),
b) the cell wall (9) is irradiated on the transverse face which lies opposite the transverse face which forms the support of the cell wall (9) in the middle by an irradiation device through an optical glass window (11) and is observed at a right angle to the optical axis of the irradiation device through a further optical glass window (11) by an observation device (6, 6a),
c) the common focus of the irradiation device and the focus of the observation device can be displaced in a motorized fashion over the spatial inner region of the cell wall (9) to an arbitrary point by a control apparatus,
d) the face of the cell wall (9) which lies opposite the optical glass window (11) through which the irradiation device radiates has a further optical glass window (11) in the middle, this face of the cell housing (9) having a congruent nanocarbon layer (5) externally covering it,
e) the face of the cell wall (9) in which the optical glass window (11), through which the optical axis of the observation device extends, is situated is monitored in respect of its temperature by two thermistors (8).

The apparatus can further include:
an electrode (19) of an electrical voltage source is respectively applied to the two end sides of the cuboid cell wall (9), each of these electrodes (19) consisting of an outer and an associated inner electrode,
an arrangement (7) with which various filters can be switched into the beam path is provided in the optical axis of the observation device,
the irradiation device is a laser (10), and the observation device is a digital video camera (6) having a microscope objective (6a),
a storage container (12) of washing solutions or diluting solutions with a connected dosing pump (13) is provided on one end side of the cuboid cell wall (9), and a compensation container (14) for sample liquid is provided on the other end side, an additional sample container (15) with an associated dosing pump (16) being provided, and liquids being deliverable in a dosed fashion from the storage container (12) and the sample container (15) to a mixing chamber (17), and a miniature pH measuring probe being fitted in the region of the mixing chamber (17).

This object is also achieved by:
A method for particle tracking analysis with the aid of scattered light of particles (23) of the order of magnitude of nanometers of a suspension in a cell wall (9), having the following features:
a) the cell wall (9) is positioned in a defined way by means of vibration dampers (4), the cell wall (9) consisting of black glass in which optical glass windows (11) for the detection process are formed,
b) the cell wall (9) is irradiated through an optical glass window (11) by means of an optical irradiation device, and is observed at a right angle to the optical axis of the irradiation device through a further optical glass window (11) by an observation device,
c) the focus of the irradiation device and the focus of the observation device are displaced in a motorized fashion in a particular region of the cell wall (9) to the same point by optimizing the imaging property in relation to one or more particles (23) in this region, the electrophoresis effect being kept apart clearly from the electroosmosis effect,
d) the control parameters thereby obtained are used as a basis for the representation of particles (23), the zeta potential of the sample, its conductivity and its pH being metrologically detected simultaneously.

The method can be further characterized in that:
the irradiation device consists of a laser (10) and the observation device consists of a digital video camera (6) having a microscope objective,
the thermal effect of the light irradiation of the irradiation device on the suspension is minimized in that it is made possible by a further glass window (11), lying opposite the optical glass window (11) which allows entry of the light of the irradiation device into the cell wall (9), for the light beam of the irradiation device to emerge from the cell wall (9) and this light beam can give up its heat in a nanocarbon layer (5),
a pattern analysis in the case of particles (23) of the size range of nanometers with the aid of scattered light can be carried out for the first time in the world, and a computer program having a program code for carrying out the method steps as claimed in one of claims 6 to 9 when the program is run on a computer, as well a machine-readable medium having the program code of a computer program for carrying out the method when the program is run on a computer.

BRIEF DESCRIPTION OF THE SEVERAL VIEWS OF THE DRAWINGS

The apparatus according to the invention will be described in more detail below. In detail:
FIGS. 4A and 4B show a representation to illustrate the measurement principle.
FIG. 5 shows a flowchart of a processing method.

DETAILED DESCRIPTION OF THE INVENTION

Figure 1A:
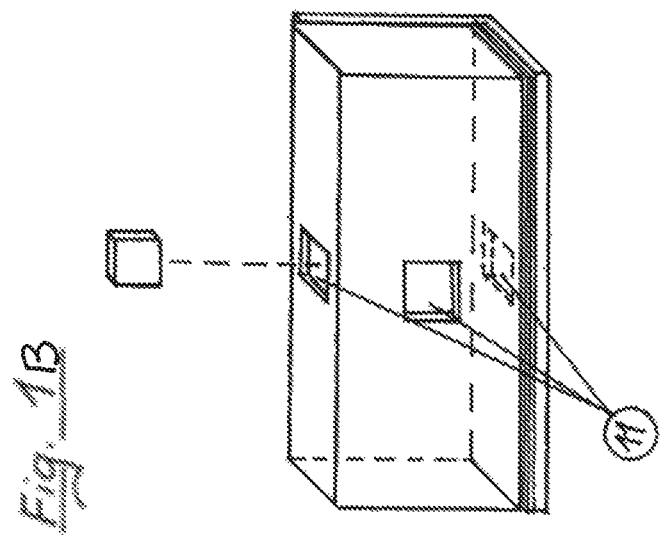
FIG. 1A shows a cross section of the cell wall and FIG. 1B shows a three-dimensional view of the cell wall.
Figure 1B:
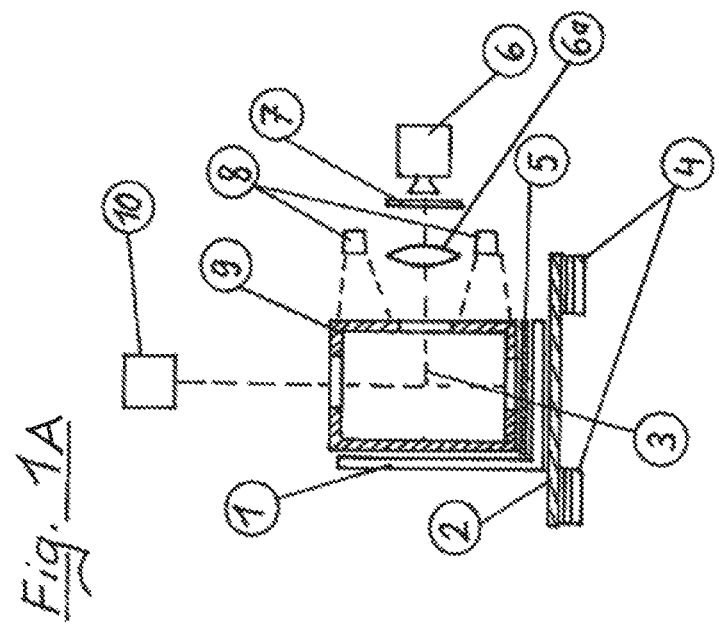

FIG. 1A shows a cross section of the cell wall and FIG. 1B shows a three-dimensional view. The cell wall 9, which is configured rectangularly in cross section and contains the suspension to be studied, is placed with its cross section at the midpoint of the left-hand part of this figure. Cell wall 9 is held on the left-hand side by a heating and cooling element 1, which is L-shaped in cross section and the function of which will be described in more detail below. The entire apparatus is mounted on a standard base 2, which is in turn protected against shaking from the region of the surroundings by means of vibration-damping elements 4. In order to illuminate the suspension, a laser 10 is provided on the upper side of the cell wall 9, the main beam profile of which laser is indicated by a dashed line which extends centrally through the cell wall 9. After it has crossed the cell wall 9 through an opening, which is represented as being transmissive, the beam of the laser 10 strikes the opposite side of the cell wall 9 and is absorbed and thermally neutralized there by a nanocarbon layer 5, which likewise lies behind an opening represented as being transmissive. The function of the layer 5 will be further described below. At a right angle to this dashed line, the optical axis 3 of a digital video camera 6 and of a microscope objective 6a is indicated, likewise by means of a dashed line. This optical axis 3 also passes through an opening represented as being transmissive. At the point of intersection of these two dashed lines, the particles to be studied can be observed. Provided in the beam path of the digital video camera 6, there is a filter changer 7 which, respectively according to requirements, can place various color filters in front of the objective of the camera 6. Furthermore, a microscope objective 6a is arranged in the beam path of the digital video camera. On this side of the part of the cell wall 9 observed by the digital video camera 6, two thermistors 8 which register the development of heat of the cell wall are provided.

A three-dimensional view of the cell wall 9, from which the arrangement of the openings shown in FIG. 1A can be seen better is represented in FIG. 1B. The openings described above represent optical glass windows 11 which are sintered into the cell wall 9. The heating and cooling element 1 and the nanocarbon layer 5 are used in order to achieve a uniform temperature distribution in the cell. This layer 5 immediately dissipates the thermal radiation, caused by the laser 10 when the laser emerges from the cell wall 9 through the window 11, laterally and into the cooling element 1. Thermal convection in the cell is therefore substantially avoided. Thermal convection is competitive with the particle diffusion and electrophoretic movement which are to be measured in the field, and is therefore to be avoided.

Figure 2:
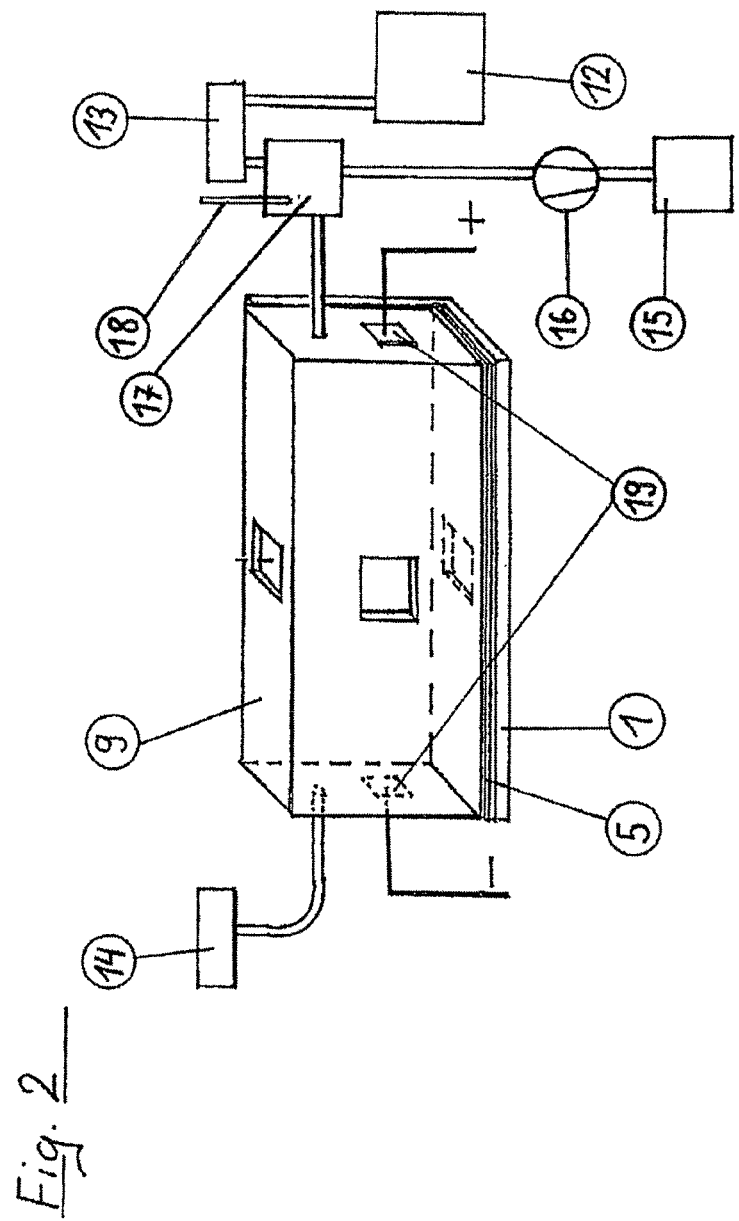
FIG. 2 shows a three-dimensional view of the cell with peripheral arrangements.

FIG. 2 shows a three-dimensional view of the cell with peripheral arrangements. Besides the known cell wall 9 with its optical glass windows 11 sintered in, heating and cooling element 1 and the nanocarbon layer 5 applied on the bottom of the cell wall 9 can be seen here. A negative and a positive electrode 19 are respectively fitted on the two narrow sides of the cell wall 9. These electrodes 19 respectively consist of two electrodes, respectively an outer electrode outside the cell wall 9 and an associated inner electrode, from which the relevant electric field is tapped, lying inside the cell wall 9. In this way, it is possible to compensate for perturbing effects such as bubble formation. Electrophoretic movement of particles to be studied can thereby be induced by applying a controllable electrical voltage. Two dosing pumps 13 and 16 for supplying washing or diluting solution, or suspension, from a storage container 12 or 15, respectively, are provided on the right-hand narrow side of the cell wall 9. A compensation container 14 is fitted on the left-hand narrow side of the cell wall 9. On the right-hand narrow side, there is likewise a miniature mixing chamber 17 for receiving the sample suspension from 12 or from a syringe. In the case of simultaneous dosing of sample and diluting solution from the containers 12 and 15, defined dilution of the samples is achieved. A miniature pH measuring probe 18 is fitted at an outlet of the mixing chamber 17.

Figure 3:
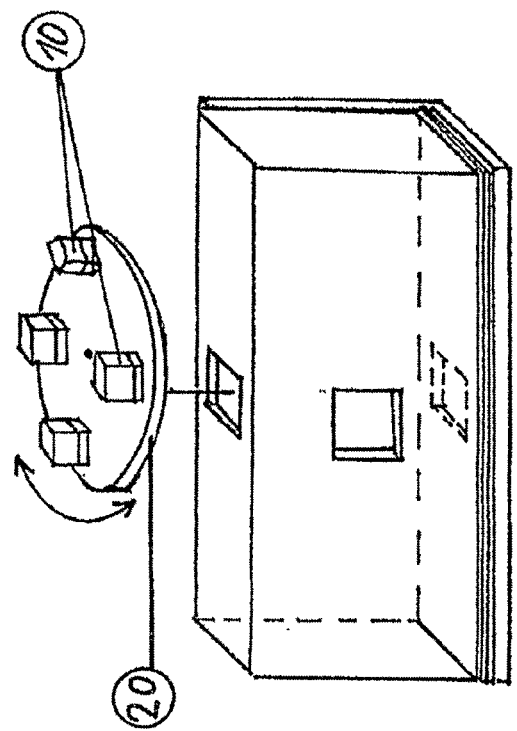
FIG. 3 shows a three-dimensional view of the cell in a special embodiment.

FIG. 3 shows a spatial view of the cell in a special embodiment. Here, the way in which a particular laser 10 from a multiplicity can selectively be chosen and rapidly used, respectively according to requirements, in order to study a particular suspension, by means of a rotatable changer disk 20 is shown in principle and by way of example. The changer disk 20 may also be a horizontally mobile displacement carriage.

FIGS. 4A and 4B show a representation to illustrate the possibilities of the measurement principle according to the invention. With reference to the example of a particle 23, represented as an irregular conglomerate in FIG. 4A, having a diameter of 100 nm, it is shown here that this particle 23, when it has moved through a distance delta x in a time delta t, is not only revealed, in FIG. 4B, as a size peak 21 in the study but also that a broader, smaller size peak 22, which in the past has usually remained unobserved, can likewise be indicated accurately. This is because, as already mentioned, the smaller peak 22 has in the past usually been overlooked or ascribed to the effect of a smaller particle, with the method according to the invention it is possible to discover that the smaller peak 22 is to be ascribed to the effect of the rotation of the particle 23.

This is overall automatic evaluation, for the first time, of the dynamic scattered light pattern analysis. In this case, the number of primary particles, agglomerates and aggregates is determined. Evaluation of the scattered light shape parameters (secondary shape parameters), evaluation of the intensity of the particle scattered light, of the particle scattered light area, and all dynamic values thereof, are carried out. The fluctuation width of these parameters is obtained therefrom. Evaluation of the proportions of different particle types is furthermore possible (example, milk: milk droplets, milk exosomes, caseins (example, mixture of particles and nanobubbles)).

The complex analysis of the described movement processes requires a special control program.

FIG. 5 shows a flowchart of the processing method according to the invention.

The essential method steps which can be distinguished during the measurement and analysis with the apparatus according to the invention are presented in FIG. 5.

After starting and putting in operation, the apparatus or the instrument is initialized. In this case, all sensors and actuators are addressed and their reference values are read out. If reference values, determined in this way, of individual instrument components lie in the range specified for them, the instrument is ready for a measurement.

As preparation for a sample application, reference measurements with pure water and subsequently with a known, accurately defined sample are initially carried out. For example, a defined diluted particle size standard is suitable for this purpose. The reference measurements give information about the performance of the instrument and about whether the specifications of the instrument are being complied with. This relates to the first three symbols of the flowchart. The sample application according to the fourth symbol of the flowchart of FIG. 5 is carried out either manually or by a separate automated application system. After the sample application, camera parameters are determined and electronic filter settings are carried out according to the fifth symbol of the flowchart. With the aid of measured parameters, such as the conductivity and the temperature, inferences are made about the quality of the filling and the adapted concentration. Parameters from the pre-analysis of images are also used for this, changes of the objects as a function of time also being taken into account. These so-called quality parameters such as image brightness, number of objects detected, as well as the shape and size of the objects, can provide information about the presence of bubbles or other perturbing reflections. In the event of an excessively high concentration of particles, a high image brightness is thus obtained. In this case, the sample must be diluted and transferred into the measurement cell again.

After the testing of the quality parameters of the sample filling, a video sequence is recorded and is stored according to the sixth symbol of acquisition of the flowchart.

In the seventh symbol of video analysis, the video sequence is evaluated either in real time or with a time delay. To this end, the video sequence is decomposed into its individual images, the objects of each individual image are localized and their object properties, such as the brightness, size or the shape, are determined.

According to the eighth symbol, the individual objects are combined to form so-called traces over the individual images, which are linked besides the data of the offset with the data of the object properties.

In the result representation according to the ninth symbol, a size distribution (i.e. a histogram) is represented. Furthermore a so-called multidimensional evaluation is carried out by methods of multivariate statistics with inclusion of the object properties from the image. By the multidimensionality (offset, size of the objects, brightness and time variation), a sample can be subdivided into subgroups. The presence of a plurality of different sample constituents can therefore be inferred. Furthermore, the evaluation provides information about measurement artefacts. The result is then cleaned of these artefacts. For example, this may involve the component of translational diffusion, particularly of larger particles. After the end of the evaluation and the result representation, either the sample may be evaluated again, for example with other filter parameters, or a new sample may be injected and measured. Furthermore, the program may be ended and the instrument may be shut down with a sequence (washing, cleaning, disinfection).

LIST OF REFERENCES 1 heating and cooling element (Peltier element)
2 stand base
3 optical reference line
4 vibration-damping element
5 nanocarbon layer
6 digital video camera 6a microscope objective
7 filter changer
8 thermistor
9 cell wall
10 laser
11 optical glass window
12 storage container for diluting solution
13 dosing pump for the diluting solution
14 compensation container
15 sample container
16 dosing pump for the sample
17 mixing chamber
18 miniature pH measuring probe
19 electrodes
20 changer disk
21 size peak as indication of translation
22 size peak as indication of rotation
23 particle

The invention claimed is:

1. An apparatus for detecting and characterizing particles in liquids of all types of the order of magnitude of nanometers of a suspension in a cell wall, the apparatus comprising:
 a) a cell wall of rectangular cross section comprising black glass with optical windows and an L-shaped heating and cooling element applied to a longitudinal face and an adjoining transverse face, the transverse face of the cell wall bearing on a stand base which is mounted on vibration dampers,
 b) the cell wall is configured to be irradiated on a transverse face which lies opposite the transverse face which forms the support of the cell wall in the middle by an irradiation device through an optical glass window and is observed at a right angle to the optical axis of the irradiation device through a further optical glass window by an observation device,
 c) a focus of the irradiation device and a focus of the observation device, each of which can be displaced in a motorized fashion over the spatial inner region of the cell wall to an arbitrary point by a control apparatus,
 d) wherein the face of the cell wall which lies opposite the optical glass window through which the irradiation device radiates has a further optical glass window in the middle, this face of the cell housing having a congruent nanocarbon layer externally covering it,
 d) wherein the face of the cell wall in which the optical glass window, through which the optical axis of the observation device extends, is configured to be monitored in respect of its temperature by two thermistors.

2. The apparatus as claimed in claim 1, further comprising an electrode on each end side of the cell wall, wherein an electrical voltage source is respectively applied to the two end sides of the cell wall, each electrode consisting of an outer and an associated inner electrode.

3. The apparatus as claimed in claim 2, further comprising a filter changer having various filters that can be switched into the beam path, wherein the filter changer is provided in the optical axis of the observation device.

4. The apparatus as claimed in claim 2, wherein the irradiation device is a laser, and the observation device is a digital video camera having a microscope.

5. The apparatus as claimed in claim 2, further comprising:
 a storage container for washing solutions or diluting solutions with a connected dosing pump on one end side of the cell wall, and a compensation container for sample liquid on the other end side,
 a sample container with an associated dosing pump, configured to deliver liquids in a dosed fashion from the storage container and the sample container to a mixing chamber, and
 a miniature pH measuring probe fitted in the region of the mixing chamber.

6. A method for particle tracking analysis with the aid of scattered light of particles of the order of magnitude of nanometers of a suspension in a cell wall, the method comprising:
 a) positioning the cell wall on vibration dampers, the cell wall comprising black glass having optical glass windows,
 b) irradiating the cell wall through an optical glass window by means of an optical irradiation device, and observing at a right angle to the optical axis of the irradiation device through a further optical glass window by an observation device,
 c) adjusting the focus of the irradiation device and the focus of the observation device in a motorized fashion on a particular region of the cell wall to the same point by optimizing the imaging property in relation to one or more particles in this region, wherein an electrophoresis effect is distinguishable from an electroosmosis effect,
 d) utilizing the control parameters thereby obtained as a basis for the representation of particles, and measuring a zeta potential of the sample, its conductivity and its pH, wherein the measured information is metrologically detected simultaneously.

7. The method as claimed in claim 6, wherein the irradiation device comprises a laser and the observation device comprises a digital video camera having a microscope objective.

8. The method as claimed in claim 7, wherein a thermal effect of the light irradiation of the irradiation device on a suspension is minimized by a further glass window, lying opposite the optical glass window, which allows entry of the light of the irradiation device into the cell wall, wherein a light beam of the irradiation device can emerge from the cell wall and this light beam can release its heat on a nanocarbon layer.

9. The method as claimed in claim 6, further comprising analyzing a pattern in the particles based on the size range of nanometers with the aid of scattered light.

10. The method as claimed in claim 6, wherein during the measurement and analysis with the apparatus as claimed in claim 1, distinction is to be made between the following method steps:
   a) after starting and putting in operation, initialize sensors and actuators and obtain their reference values, wherein reference measurements are obtained with pure water and/or a defined sample initially being carried out for sample recording,
   b) after the sample recording, determine camera parameters and adjust electronic filter,
   c) after testing of the quality parameters of the sample filling, record a video sequence and store according to the symbol of the acquisition,
   d) as the next method step, evaluate the video sequence either in real time or with a time delay,
   e) according to the next method step, join together individual objects to form traces over the individual images, which are linked besides the data of the offset with the data of the object properties,
   f) in the result representation, provide a size distribution and carry out a multidimensional evaluation using multivariate statistics,
   g) as a consequence, either the sample is evaluated again with different filter parameters or a new sample is measured, and
   h) the apparatus is switched off.

11. A computer program having a program code for carrying out the method steps as claimed in claim 6 when the program is run on a computer.

12. A machine-readable medium having the program code of a computer program for carrying out the method as claimed in claim 6 when the program is run on a computer.

* * * * *